United States Patent
Igney et al.

(10) Patent No.: US 8,125,220 B2
(45) Date of Patent: Feb. 28, 2012

(54) MAGNETIC INDUCTION TOMOGRAPHY SYSTEM AND METHOD

(75) Inventors: Claudia Hannelore Igney, Aachen (DE); Robert Pinter, Aachen (DE); Olaf Such, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 910 days.

(21) Appl. No.: 12/097,529

(22) PCT Filed: Dec. 14, 2006

(86) PCT No.: PCT/IB2006/054834
§ 371 (c)(1),
(2), (4) Date: Jun. 14, 2008

(87) PCT Pub. No.: WO2007/072343
PCT Pub. Date: Jun. 28, 2007

(65) Prior Publication Data
US 2008/0258717 A1  Oct. 23, 2008

(30) Foreign Application Priority Data
Dec. 22, 2005  (EP) .................................. 05112737

(51) Int. Cl.
*G01B 7/14* (2006.01)
*G01R 33/12* (2006.01)
*G01N 27/82* (2006.01)
(52) U.S. Cl. .... 324/240; 324/243; 324/228; 324/207.15
(58) Field of Classification Search .................. 324/240, 324/243, 228, 207.15
See application file for complete search history.

(56) References Cited

U.S. PATENT DOCUMENTS
5,144,236 A  9/1992  Strenk

FOREIGN PATENT DOCUMENTS
JP      04093783 A1   3/1992
WO   2004015435 A1   2/2004
WO   2005057467 A2   6/2005

OTHER PUBLICATIONS

Hermann Scharfetter, et al: A New Type of Gradiometer for the Receiving Circuit of Magnetic Induction Tomography (MIT) Physiological Measurement Institute of Physic Publishing, vol. 26, No. 2, Apr. 1, 2005, pp. S307-S318.

Yu Z Z, et al: Electromagnetic Inductance Tomogdraphy (EMT) Sensor, Electronics and Image Reconstruction Algorithm for a System with a Rotatable Parallel Excitation Field, IEEE Proceedings, Science Measurement and Technology, vol. 145, No. 1, Jan. 6, 1998, pp. 20-25.

Robert Merwa, et al: Numerical Solution of the General 3D Eddy Current Problem for Magnetic Induction Tomography, (spectroscopy) Physiological Measurement, Institute of Physics Publishing, vol. 24, No. 2, May 1, 2003, pp. 545-554.

Greig C. Scott, et al: Rotating Frame RF Current Density Imaging, MRI Technique in Which the B1 Field Rotate From Improved Resolution, MRM vol. 33, 1995, pp. 355-369.

Olaf Dossel: Bildgebende Verfahren in der Medizin Von der Technik zur Medizinischen Anwendung, Springer Verlag, 2000, chapter 9,10 and chapter 11.6 and Translation.

*Primary Examiner* — Reena Aurora

(57) ABSTRACT

A magnetic induction tomography system and method for studying the electromagnetic properties of an object includes generator coils adapted for generating a primary magnetic field, and sensor coils adapted for sensing a secondary magnetic field. Actuators provide relative movement between the generator coils and/or the sensor coils on the one hand and the object to be studied on the other hand.

15 Claims, 6 Drawing Sheets

MAGNETIC INDUCTION TOMOGRAPHY SYSTEM AND METHOD

Figure 1:
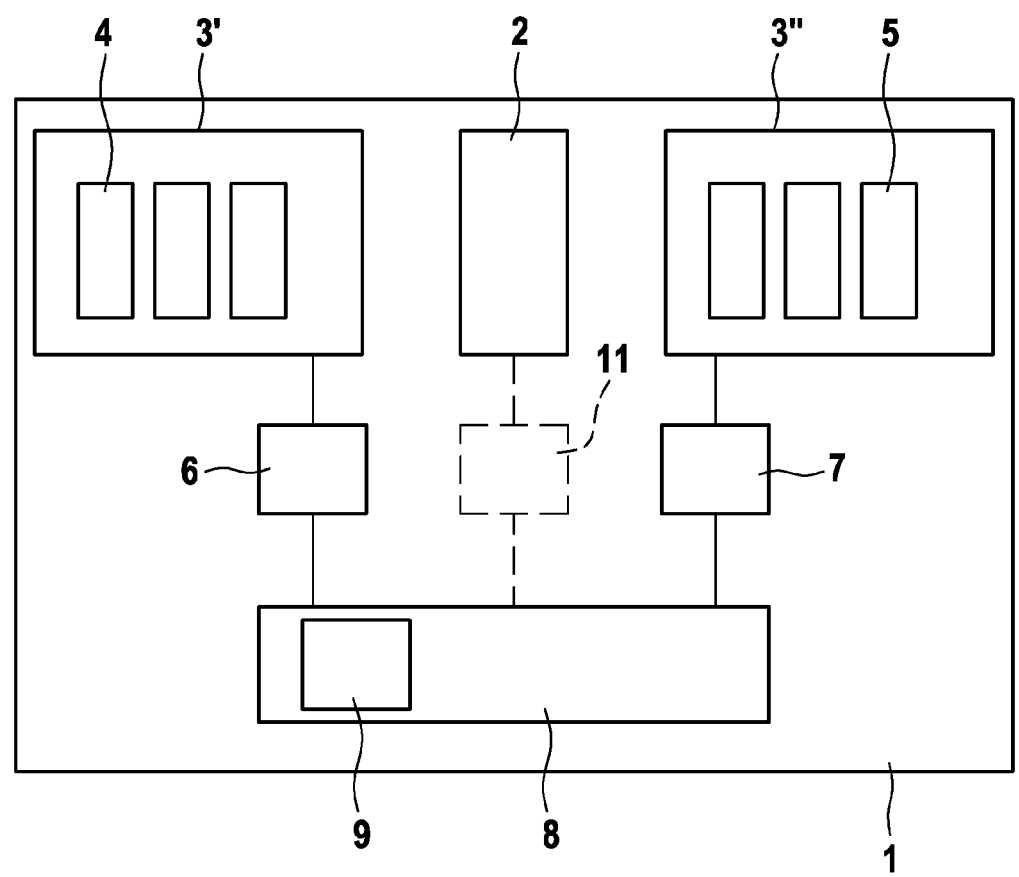

The present invention relates to a magnetic induction tomography system and method for studying the electromagnetic properties of an object.

Magnetic induction tomography (MIT) is a noninvasive imaging technique with applications in industry and for medical imaging. In contrast to other electrical imaging techniques, MIT does not require direct contact of the sensors with the imaged object.

MIT applies a magnetic field from one or more generator coils (also called excitation coils) to induce eddy currents in the material to be studied. In other words, the scanning region is excited with a time varying magnetic field. The presence of conductive and/or permeable material distorts the energizing field within. The perturbation of said primary magnetic field, i.e. the secondary magnetic field resulting from the eddy currents, is detected by a number of sensor coils (also called measurement coils, detection coils or receiving coils). Sets of measurements are taken and used to recover the position, the shape and the electromagnetic properties of the object. MIT is sensitive to all three passive electromagnetic properties: electrical conductivity, permittivity and magnetic permeability. As a result, for example, the conductivity contribution in a target object can be reconstructed. In particular MIT is suitable for examination of biological tissue, because of the value of magnetic permeability of such tissue $\mu_R \approx 1$.

Image reconstruction with MIT using multiple measurements is an ill-posed, under-determined and non-linear inverse problem, which can be estimated by linearizing the problem, as explained in more detail in Olaf Dössel: "Bildgebende Verfahren in der Medizin. Von der Technik zur medizinischen Anwendung", Springer-Verlag, 2000, chapter 9.10 and chapter 11.6. Therefore the following equation is obtained:

$$S(x_0)*(x-x_0)=b-b_0$$

where S: sensitivity matrix (lead field matrix), x: image vector (conductivity), $x_0$: initial conductivity value, b: measurement vector (voltages measured by means of the sensor coils) and $b_0$: initial measured vector at the conductivity $x_0$. For the following it is assumed that the sensitivity matrix (transfer matrix) S can be written as:

$$Sx=b$$

The sensitivity matrix has to be inverted:

$$x=S^{-1}b$$

The inverting can be carried out using different inversion methods, e.g. using Moore-Penrose pseudo-inverse (MPS), Tikhonov Regularization with Generalized Cross-Validation technique (TCGV) or Tikhonov Regularization with non-negativity constraint (TNN). The inverting of the sensitivity matrix S can be carried out more easily, the solution is more stabile, and the spatial resolution of the reconstructed image is higher, if a large number of independent measurement information (b-values) exist.

In other words, a preferably large number of (independent) measurements is needed. A MIT system comprising E generator coils and M sensor coils allows E(M−1) measurements, where only E(M−1)/2 measurements are independent. Therefore, prior art solutions always suggest to increase the number of measurements by using an increased number of coils. This leads to very large and complex MIT systems. Furthermore such systems are very expensive due to the required operating equipment.

It is an object of the present invention to provide a high resolution MIT technique without the need of increasing the number of coils. This object is achieved according to the invention by a magnetic induction tomography system for studying the electromagnetic properties of an object, the system comprising one or more generator coils adapted for generating a primary magnetic field, said primary magnetic field inducing an eddy current in the object, further comprising one or more sensor coils adapted for sensing a secondary magnetic field, said secondary magnetic field being generated as a result of said eddy current, and further comprising means for providing a relative movement between one or more generator coils and/or one or more sensor coils on the one hand and the object to be studied on the other hand.

The object of the present invention is also achieved by a magnetic induction tomography method for studying the electromagnetic properties of an object, the method comprising the steps of generating a primary magnetic field by means of one or more generator coils, said primary magnetic field inducing an eddy current in the object, and sensing a secondary magnetic field by means of one or more sensor coils, said secondary magnetic field being generated as a result of said eddy current, and providing a relative movement between one or more generator coils and/or one or more sensor coils on the one hand and the object to be studied on the other hand.

The object of the present invention is also achieved by a computer program for operating a magnetic induction tomography system for studying the electromagnetic properties of an object, the system comprising one or more generator coils adapted for generating a primary magnetic field, said primary magnetic field inducing an eddy current in the object, one or more sensor coils adapted for sensing a secondary magnetic field, said secondary magnetic field being generated as a result of said eddy current, and means for providing a relative movement between one or more generator coils and/or one or more sensor coils on the one hand and the object to be studied on the other hand, the computer program comprising computer instructions to automatically control the movement(s) of said coil(s) and/or the movement(s) of said object, when the computer program is executed in a computer. The technical effects necessary according to the invention can thus be realized on the basis of the instructions of the computer program in accordance with the invention. Such a computer program can be stored on a carrier such as a CD-ROM or it can be available over the internet or another computer network. Prior to executing the computer program is loaded into the computer by reading the computer program from the carrier, for example by means of a CD-ROM player, or from the internet, and storing it in the memory of the computer. The computer includes inter alia a central processor unit (CPU), a bus system, memory means, e.g. RAM or ROM etc., storage means, e.g. floppy disk or hard disk units etc. and input/output units. Alternatively, the inventive method could be implemented in hardware, e.g. using one or more integrated circuits.

A core idea of the invention is to move the generator coil(s) and/or the sensor coil(s) with respect to the target object. By doing so, the number of independent measurements is increased without more coils being needed. As a result, the inverting of the sensitivity matrix can be carried out more easily, the solution is more stabile, and the spatial resolution of the reconstructed image is higher. Based on the suggested MIT system and method a high quality image reconstruction is possible without expensive and hard to control operating equipment.

These and other aspects of the invention will be further elaborated on the basis of the following embodiments which are defined in the dependent claims.

According to a preferred embodiment of the invention even more independent measurements are possible, if one or more generator coils and/or one or more sensor coils are arranged in an asymmetric way. Using an asymmetric arrangement of coils in combination with a relative coil movement leads to a significant increase of independent measurement information to be used in the sensitivity matrix. This embodiment comprises an asymmetric arrangement of generator coils to each other as well as an asymmetric arrangement of sensor coils to each other as well as an asymmetric arrangement of generator coils to sensor coils.

In another preferred embodiment one or more generator coils and/or one or more sensor coils are arranged in form of an array. This embodiment comprises the case, in which several generator coils are arranged in form of an array as well as the case, in which several sensor coils are arranged in form of an array as well as the case, in which one or more generator coils and one or more sensor coils are arranged in form of an array. For example a single generator coil may cooperate with an array of sensor coils or an array of generator coils may cooperate with an array of sensor coils. An arrangement of coils in form of an array lead to a faster scanning performance, since all sensor coils can obtain signals simultaneously. Furthermore the mechanical design of the system needs to be less complex, because a full 360° rotation is not necessary if a symmetric arrangement is used.

In another embodiment of the invention the moving means are adapted such that one or more generator coils and/or one or more sensor coils can perform movements independent of each other. This embodiment comprises the case of several generator coils moving independent of each other, as well as the case of several sensor coils moving independent of each other, as well as the case of one or more generator coils moving independent of one or more sensor coils. The main advantage of coils being moved independently is that every possible geometrical arrangement can be reached. In other words, all coil positions can be reached separately.

The kind of coil movement can vary depending on the geometry of the coil arrangements. In an embodiment of the invention the moving means are adapted to rotate one or more coils relative to the object to be studied, in particular to rotate one or more coils around the object. This embodiment comprises the case of rotating one or more generator coils and/or one or more sensor coils relative to the object. A rotating movement can preferably be used together with a simple circular experimental layout. Another advantage of applying a rotating movement is the easy gathering of a complete 360° set of measurement information. A complete set of measurement information can either be collected using one sensor coil moving 360° around the object or using two equally spaced sensor coils being, each moving 180° around the object, or using e.g. sixteen equally spaced sensor coils, each moving 22.5° around the object etc. Preferably the moving means are adapted to rotate the coil(s) in arbitrary small steps. After each of those steps a sensing of the secondary magnetic field is performed. For example each of the sixteen sensor coils may cover a 22.5° area by performing 10 (or 100) intermediate steps. That means, that 10 (or 100) measurements are performed during the 22.5° rotation, i.e. a single measurement is performed after a 2.25° rotation (or after a 0.225° rotation).

In another embodiment of the invention the moving means are adapted to move one or more generator coils and/or one or more sensor coils along the rotation axis, i.e. in z-direction. The main advantage of movements in z-direction is that a larger 3D-area can be examined without the object being moved. By this way, a complete scan of an object can be achieved and additional independent measuring information can be obtained using just a small number of coils.

During the MIT scan the object to be scanned is preferably stationary. However, in another embodiment of the invention the system further comprises means for moving the object to be studied relative to the one or more generator coils and/or relative to the one or more sensor coils, said means being in particular adapted for rotating the object.

It has been found, that the sensitivity of the MIT scanner, which is representative of how much voltage change is received as the result of a given conductivity change, is higher along and close to the circumference of the measuring unit, than in the center. In other words, the sensitivity of the MIT scanner, and hence the MIT scanner's resolution, is lowest towards the centre of the scanner. Thus, in other embodiments of the invention, the system comprises means for moving the object in a plane relative to the MIT scanner from a first measurement position to a second measurement position and/or means for moving the MIT scanner in a plane relative to the object to be studied. In other words, the position of the object to be studied and the MIT scanner is changed relative to each other in a single plane, preferably in a horizontal plane. As a result, the object's position relative to the scanner changes during the measurement procedure. The relative position of the object changes, such that the sensitivity in the centre of the scanner is improved. Additionally a larger number of independent measurement information is generated, resulting in a higher image quality.

In another embodiment of the invention different coils are used as generator and/or sensor coils. Preferably, a number of generator coils and/or a number of sensor coils are used, which exhibit different coil sizes. In particular, the diameters of the generator and/or sensor coils and/or other coil parameters, like the diameter and/or length of the wire material, are different. Thus, if such different coils are used, a larger number of independent measurement information (b-values) is generated. By this means, the poor conditioning of the sensitivity matrix is improved without increasing the total number of coils. In other words, the calculation of the inverse lead-field matrix is rendered more robust, i.e. the ambiguity of the calculation is reduced. This is because the region of influence for some of the coils is limited, e.g. the region from which sensor coils receive signals and/or the region in which generator coils induce eddy currents is reduced.

Figure 2:
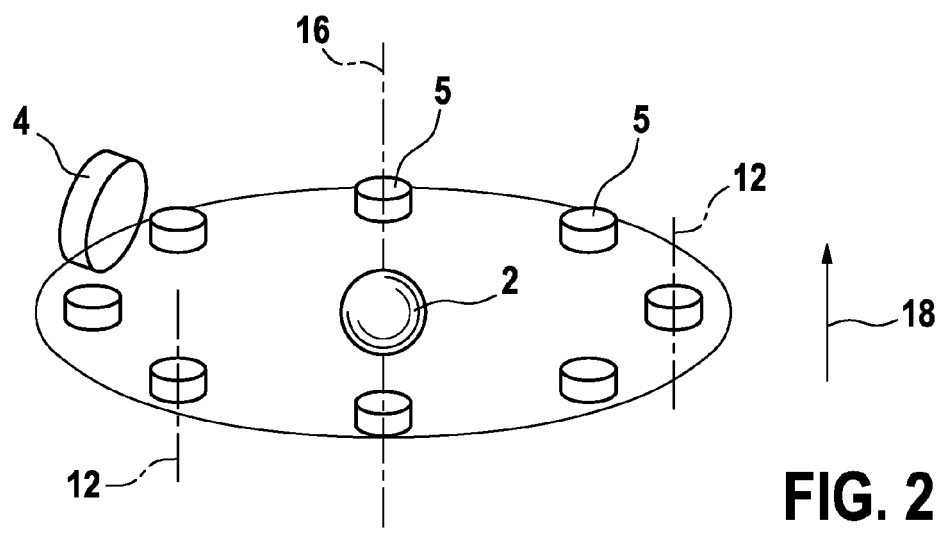
Figure 3:
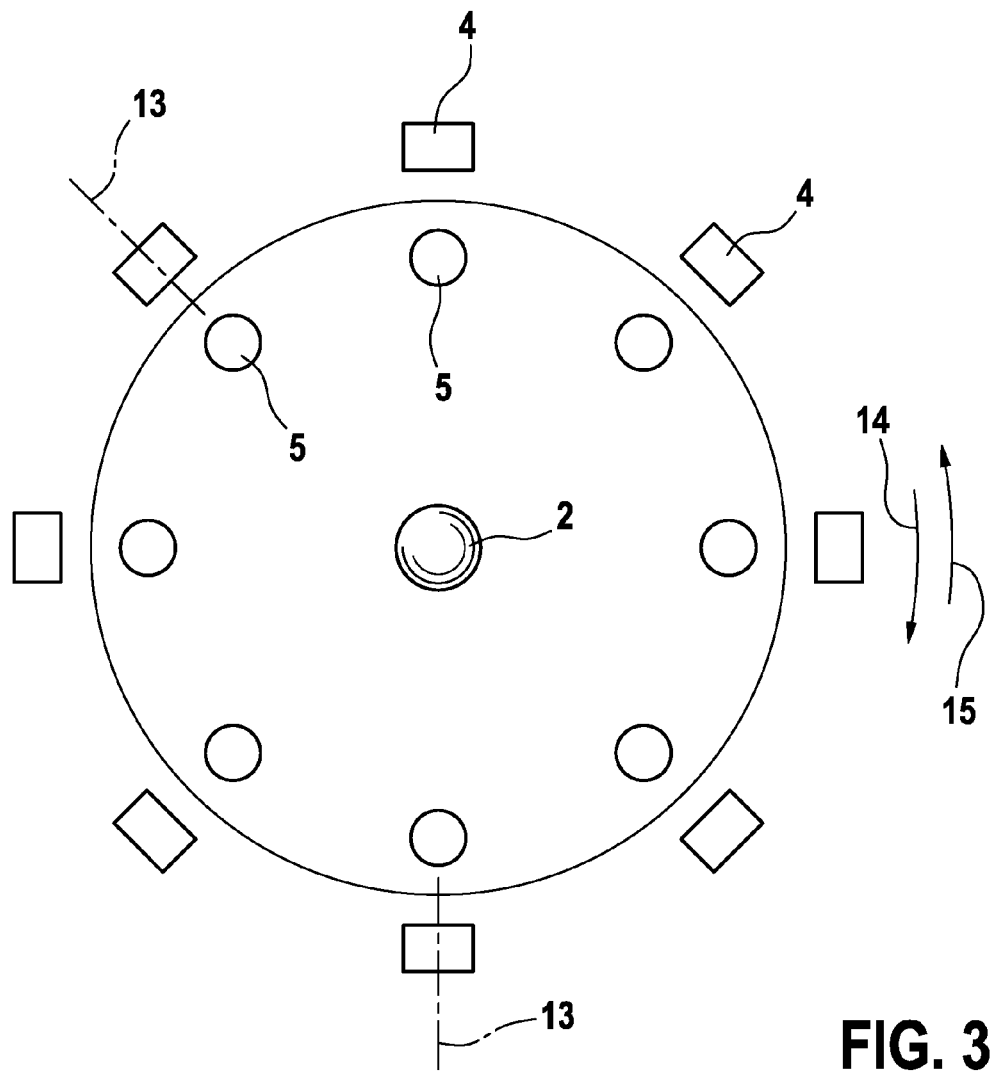
Figure 4:
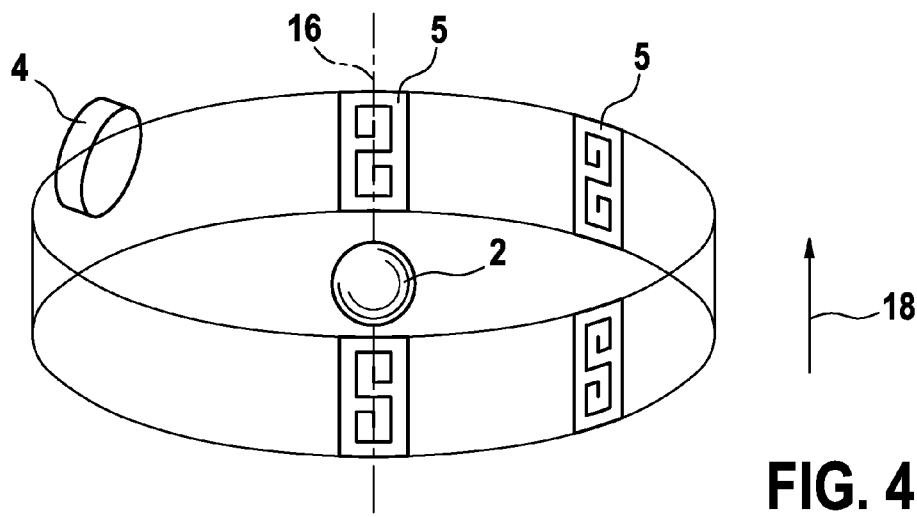
Figure 5:
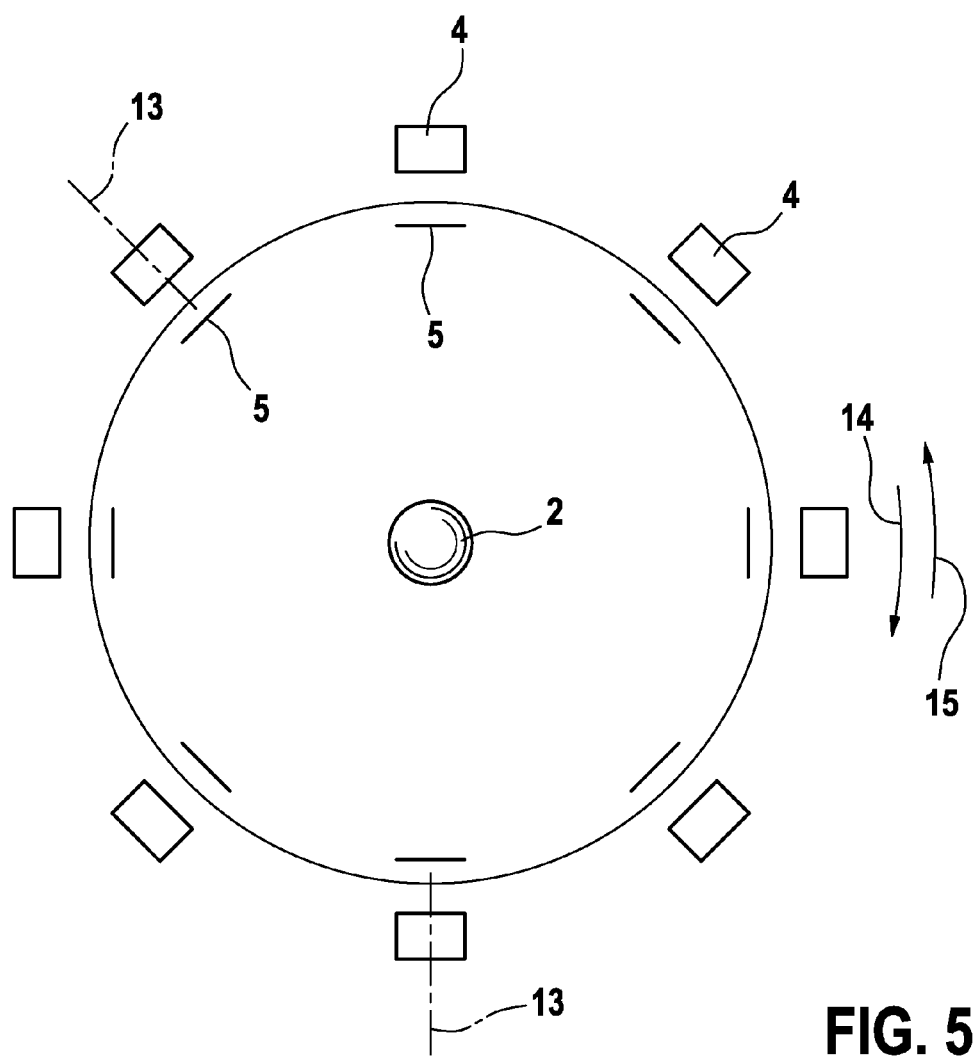
Figure 6:
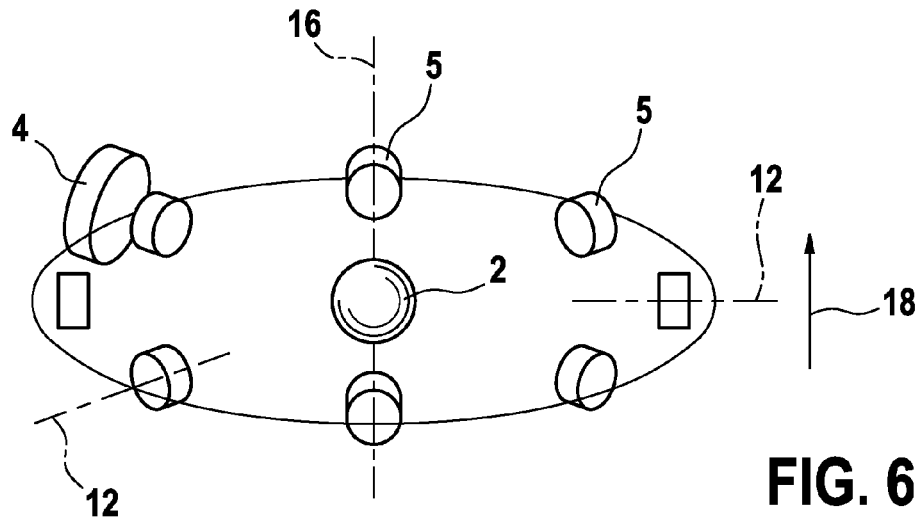
Figure 7:
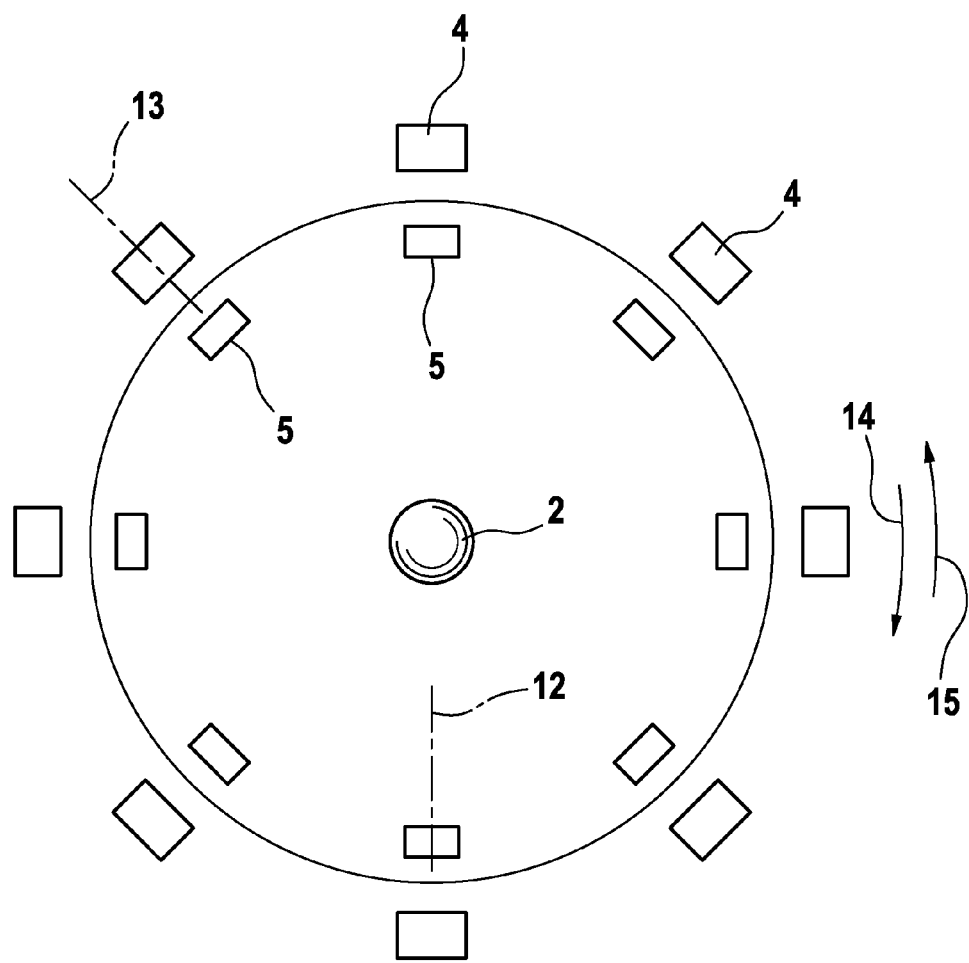
Figure 8:
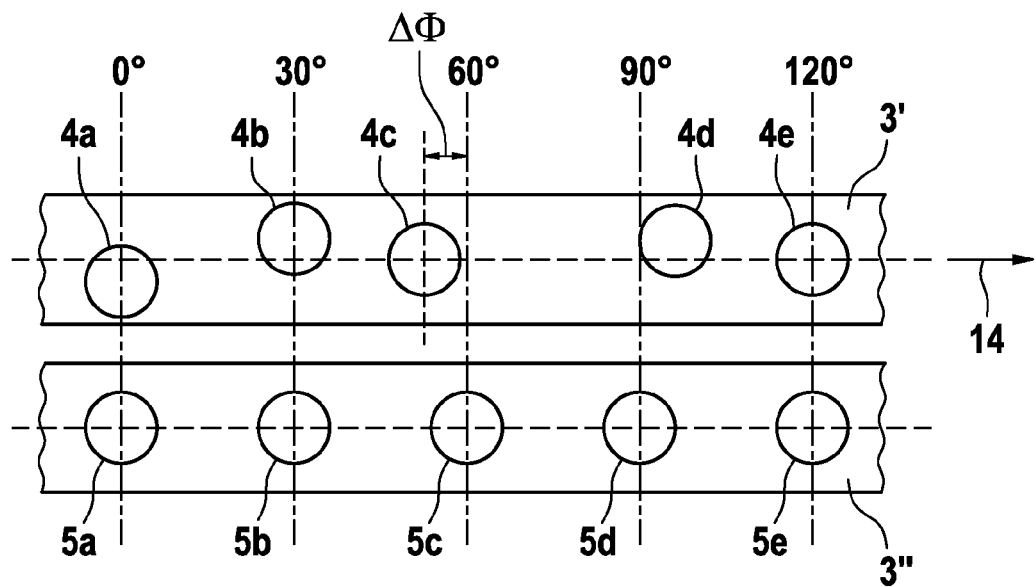
Figure 9:
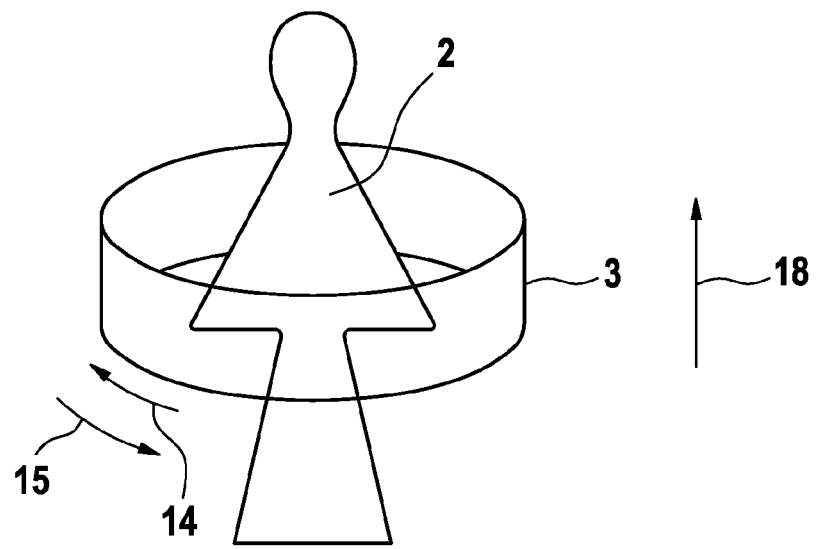
Figure 10:
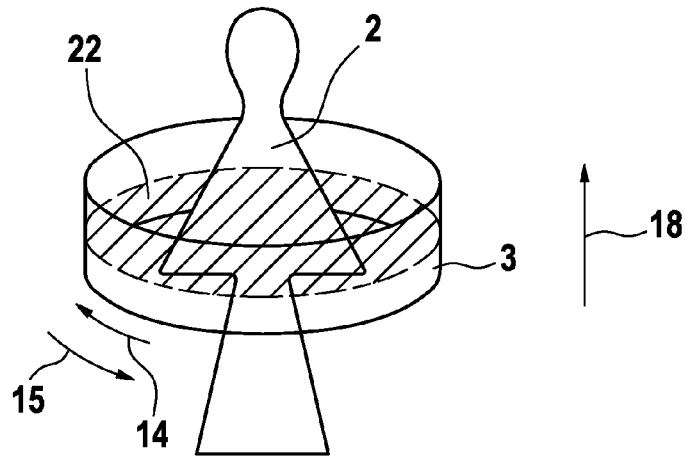
Figure 11:
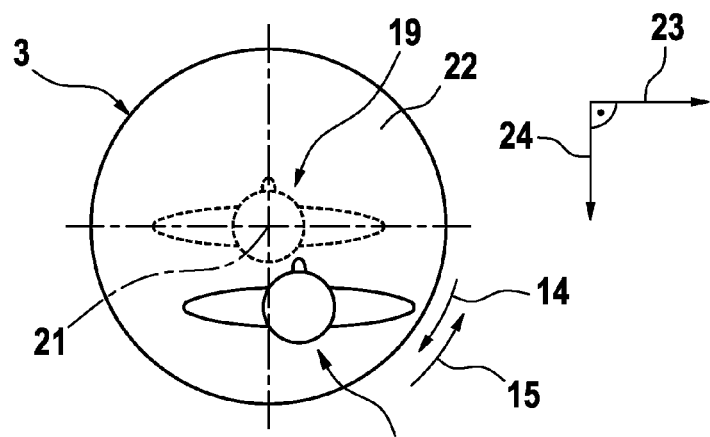
Figure 12:
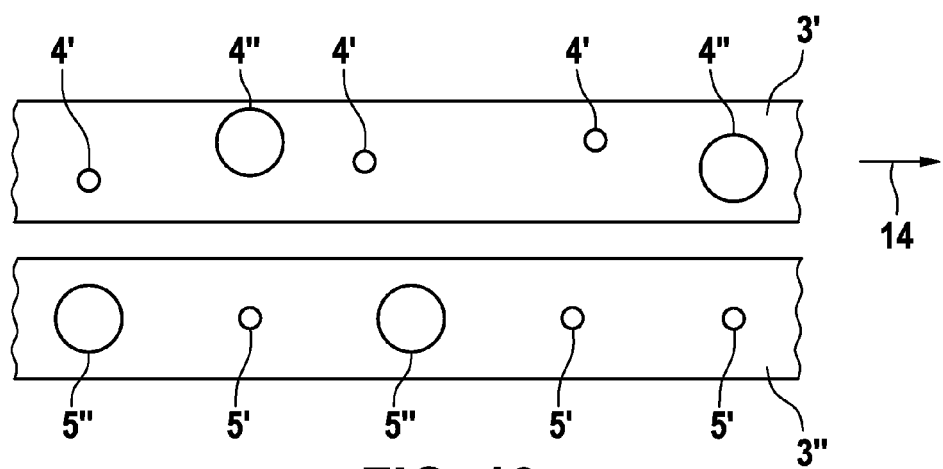

These and other aspects of the invention will be described in detail hereinafter, by way of example, with reference to the following embodiments and the accompanying drawings; in which:

FIG. 1 shows a schematic block diagram of a MIT system according to the invention, FIG. 2 shows a first coil setup ("normal alignment"), FIG. 3 shows a top view of the coil setup of FIG. 2, FIG. 4 shows a second coil setup ("planar gradiometer"), FIG. 5 shows a top view of the coil setup of FIG. 4, FIG. 6 shows a third coil setup ("primary field uncompensated setup"), FIG. 7 shows a top view of the coil setup of FIG. 6, FIG. 8 shows an asymmetric arrangement of sensor coils, FIG. 9 shows a measuring unit moveable in z-direction, FIG. 10 shows a measuring unit moveable in a horizontal plane, FIG. 11 shows a displacement of the object relative to the MIT scanner, and FIG. 12 shows an arrangement of coils with different sizes.

A schematic block diagram of a MIT system 1 according to the invention is illustrated in FIG. 1. The MIT system 1 is adapted for studying the electromagnetic properties of a biological object, in particular a conductive tissue 2. The MIT system 1 comprises among others a measuring unit 3. Said measuring unit 3 comprises an excitation module 3' and a receiving module 3". The excitation module 3' comprises a power amplifier and a number of generator coils 4 adapted for generating a time varying primary magnetic field, said primary magnetic field inducing an eddy current in the tissue 2. For this purpose an alternating current is fed into the generator coils 4. The receiving module 3" comprises a measuring amplifier and a number of sensor coils 5 adapted for sensing a secondary magnetic field, said alternating secondary magnetic field being generated as a result of said eddy current. The MIT system 1 further comprises an electrically driven actuator 6 adapted for moving one or more generator coils 4 relative to the tissue 2 and an electrically driven actuator 7 adapted for moving one or more sensor coils 5 relative to the tissue 2. The actuators 6, 7 are connected to the measuring unit 3 in order to control the coil movements. Both actuators 6, 7 are connected to a central control unit 8, from which they are controlled.

The control unit 8 comprises a computer system 9 with functional modules or units, which are implemented in form of hardware, software or in form of a combination of both hardware and software. The computer system 9 may comprise a microprocessor or the like and a computer program in form of software, which can be loaded into the computer. Alternatively the computer program is realized in form of a hardwired computer code. The computer program comprises computer instructions in order to automatically control the movement(s) of said coil(s), when the computer program is executed in the computer system 9.

During the MIT scan the tissue 2 to be examined is stationary. In another embodiment of the invention the MIT system 1 further comprises an actuator 11 adapted for moving the tissue 2 relative to the one or more generator coils 4 and/or relative to the one or more sensor coils 5. Said actuator 11 is controlled by the control unit 8 as well. The actuator 11 and the connection between the actuator 11 and the control unit 8 is illustrated in FIG. 1 using dashed lines.

The generator coils 4 are preferably adapted to operate with excitation frequencies from 100 kHz to 20 MHz. In a preferred embodiment of the invention the generator coils 4 are operated at multiple frequencies to allow "sweeping". For example a number of generator coils are operated at 2 MHz and at 5 MHz at the same time by using a non-sinusoidal waveform, e.g. a rectangular waveform, for the current to be fed into the generator coils 4. From the resulting measurement information the different frequency information is extracted using fast fourier transformation (FFT). For this purpose the measuring unit 3 is connected to a readout unit (not shown), which is preferably a data acquisition unit (data logger) combined with a microprocessor or another computer means. Since different sorts of tissue show different behaviour with respect to different excitation frequencies, this approach leads to additional information about the object under investigation. Alternatively a number of first generator coils 4 are operated at 2 MHz and at the same time a number of second generator coils 4 are operated at 5 MHz. Alternatively different excitation frequencies may be used successively, i.e. in a first measuring cycle, the generator coils 4 are operated e.g. at 2 MHz and in a second measuring cycle the same generator coils 4 are operated e.g. at 5 MHz. This second approach is however slower than the first approach, but takes less effort to separate the results. The readout of all sensor coils 5 is preferably performed at the same time, i.e. at once. By this means, the measuring speed can be increased.

The present invention can be used e.g. with a normal coil alignment or with a planar gradiometer setup. In FIGS. 2 and 3 a measuring unit with normal (i.e. vertical) alignment of coils 4, 5 is illustrated. In this embodiment the measuring unit 3 comprises eight generator coils 4 and eight sensor coils 5 corresponding to say generator coils 4. For the purpose of clarity in FIG. 2 only one generator coil 4 is shown. The solenoid coils 4, 5 are circularly arranged around a tissue 2 to be scanned. The generator coils 4 and the sensor coils 5 are placed on a common plane, with the axes 12 of the sensor coils 4 orientated perpendicularly to the axes 13 of the generator coils 5. In particular the axes 13 of the generator coils 5 are radially aligned and directed towards the tissue 2, whereas the axes 12 of the sensor coils 4 are aligned in z-direction.

In FIGS. 4 and 5 a coil setup in form of a planar gradiometer is illustrated. Again the measuring unit 3 comprises eight generator coils 4 and eight sensor coils 5 corresponding to said generator coils 4. For the purpose of clarity in FIG. 4 again only one generator coil 4 and four of the eight sensor coils 5 are shown. The coils 4, 5 are circularly arranged around a tissue 2 to be scanned. The same arrangement of solenoid generator coils 4 are used as in the normal alignment. However, as sensor coils 5, planar gradiometers are used. The planar gradiometers are drawn as two rectangular spirals with opposing directions of winding.

In FIGS. 6 and 7 a measuring unit with a primary field uncompensated alignment of coils 4, 5 are illustrated. The axes 12 of the sensor coils 5 are parallel to the axes 13 of the generator coils 4. Again, for the purpose of clarity, only one generator coil 4 is shown. All solenoid coils 4, 5 are circular arranged around the tissue 2 and are placed on a common plane. For this setup the present invention brings enormous advantages with respect to high resolution imaging.

In all three embodiments generator coils 4 and/or sensor coils 5 may be arranged in form of one or more arrays, each coil array being adapted to be moved by an actuator 6, 7 at a whole. For example the eight sensor coils 5 in FIGS. 4 and 5 could be combined into one sensor coil array. As a result all eight sensor coils 5 will move relative to the tissue 2, if the actuator 7 connected to the sensor coils 5 is controlled accordingly. Alternatively the number of sensor coils 5 could be divided into two arrays of coils. Thereby each array comprises four sensor coils 5, e.g. four adjacent sensor coils 5 or four arbitrary sensor coils 5. Alternatively the number of sensor coils 5 could be divided into an arbitrary number of arrays. Each array is adapted to be moved independently.

The actuators 6, 7 are adapted to move a number of generator coils 4 and/or a number of sensor coils 5 independent of each other. In particular the actuators 6, 7 are adapted to move a single generator coil 4 or an array of generator coils 4 in one direction and (at the same time) a single sensor coil 5 or an array of sensor coils 5 in another direction, e.g. in the opposite direction.

In the circular coil arrangement the actuators 6, 7 are adapted to rotate generator and/or sensor coils 4, 5 around the tissue 2, which is located within the coil arrangement. In case of an equidistant arrangement of sensor coils 5 each sensor coil 5 has to cover a 45° area. In other words, a 360° set of measurement information can be obtained by moving the array of eight sensor coils 5 over a 45° area around the tissue. This movements are preformed by means of the actuators 6, 7 using a large number of small intermediate steps, e.g. 45 steps. As a result, a complete MIT scan is performed by a 45° rotation of the coil arrangement. Thereby a 1° resolution is achieved. The actuators 6, 7 are adapted in a way that the generator coil(s) 4 and the sensor coil(s) 5 can be rotated independently. In FIGS. 2 to 7 the rotating direction of the generator coil(s) 4 is illustrated using arrow 14 and the rotating direction of the sensor coil(s) 5 is illustrated using arrow 15. The number of intermediate steps can be chosen according to the application.

In FIG. 8 an embodiment of the invention is illustrated, in which twelve generator coils 4 and twelve sensor coils 5 are used. For clarity reasons only five generator coils 4a to 4e and five sensor coils 5a to 5e are shown. The coils are arranged in a primary field uncompensated setup, as illustrated in FIGS. 6 and 7. The arrangement of the coils 4, 5 is shown in form of two "uncoiled" strips (excitation module 3' and a receiving module 3"), which normally form a closed loop around the object 2 to be scanned. The system shows an asymmetric arrangement of generator coils 4a to 4e and a symmetric arrangement of sensor coils 5a to 5e. In other words, the sensor coils 5a to 5e are positioned equidistant to each other and there is no displacement of the sensor coils 5a to 5e in z-direction, i.e. along the rotation axis 16. Thus, the distance between two sensor coils 5 is $\phi=30°$.

The generator coils on the other hand are positioned using different kinds of offsets. In the given example generator coil 4e is positioned in a normal position without any displacement (reference position). Generator coil 4a is displaced in negative z-direction. Generator coil 4b is displaced in positive z-direction. Generator coil 4c is displaced in "horizontal" direction, showing a negative offset of $\Delta\phi=7.5°$ of its original position. Generator coil 4d is displaced in "horizontal" direction, showing a positive offset $\Delta\phi$ of its original position and at the same time is displaced in positive z-direction.

During the scanning procedure the generator coils 4, which form a single generator coil array, are rotated in rotation direction 14. The sensor coils 5 remain in their position. The rotation of the generator coils 4 are carried out in steps of 10°. During a 360° rotation of the generator coil array there are always differently positioned coil combinations, because of the asymmetric arrangement of the generator coils 4. In other words, each time the generator coil array performs a 10° movement, a generator coil 4 shows another relative position towards the corresponding sensor coil 5. This results in an increased number of independent measurements, which can be used for image reconstruction. The embodiment illustrated in FIG. 8 shall be understood as an example. Other coil displacements and/or other coil movements are possible as well. In particular it is possible to use on the one hand an asymmetric arrangement of either generator coils 4 or sensor coils 5 or a combination of asymmetrically arranged generator and sensor coils 4, 5 and on the other hand a movement of generator coils 4 or sensor coils 5 or a combined movement of generator and sensor coils 4, 5.

Another embodiment is illustrated in FIG. 9. The measuring unit 3 of the MIT system 1 is adapted to be moveable in z-direction 18. For these purpose actuators 6, 7 are provided for moving one or more generator coils 4 and/or one or more sensor coils 5 along the rotation axis 16. If, at the same time, a coil rotation is carried out, a spiral scanning is performed, and the MIT system 1 can take nonstop images as the coils 4, 5 moving across the tissue 2.

A further embodiment of the invention is illustrated in FIGS. 10 and 11. The top view (FIG. 11) shows two different measuring positions. In a first measuring position 19 (illustrated with dotted lines) the object 2 is positioned in the centre 21 of the measuring unit 3. In a second measuring position 20 the object 2 is positioned outside the centre 21 of the measuring unit 3. The displacement of the object 2 can be achieved either by moving the object 2 relative to the measuring unit 3 or by moving the measuring unit 3 relative to the object 2 or by moving both object 2 and measuring unit 3 relative to each other. The movements are achieved by means of the actuators 6, 7, the control unit 8 comprising the computer system 9 and/or the actuator 11, as described above.

The displacement is carried out in a single horizontal plane 22, i.e. without moving the object or the scanner in z-axis 18. In the second measuring position 20 the object 2 is displaced in a first horizontal direction 23 and in a second horizontal direction 24 (perpendicular to the first horizontal direction 23) within the displacement plane 22. In other words, it is assured, that the centre of the object 2 is not constantly in the insensitive area in the centre 21 of the scanner. During the scanning procedure the insensitive centre of the scanner coincides with different regions of the object 2. Areas of the object 2, which has first been scanned with a low sensitivity can thus be scanned in another measuring position using a high sensitivity. As a result, since MIT signals are obtained for different (e.g. first and second) measuring positions, MIT signals with different sensitivities are obtained, resulting in an enhanced overall MIT resolution. In an alternative embodiment (not shown) the displacement plane is not horizontally, but tilted with respect to the z-axis 18.

Another embodiment of the invention is illustrated in FIG. 12. The MIT system 1 comprises generator coils 4 of different coil size and sensor coils 5 of different coil size. The generator coils 4' with smaller diameter concentrate their electromagnetic field to the close environment. As a result, influences on the measurement results, that might originate in greater depths of the object to be studied, can be excluded. Generator coils 4" with larger diameter are used in addition to excite greater depths. Sensor coils 5' with smaller diameter exhibit a high receiving sensitivity to their close environment, while being insensitive over large distances. On the other hand, sensor coils 5" with larger diameter cover greater depths. By employing both types of coils, the advantages of both are combined, namely high sensitivity over short distances while still covering greater depths of the object to be studied. As a result a high image quality of the reconstructed picture can be obtained.

The described MIT systems 1 provide a larger number of independent measuring information. Thus, the ill-posed and non-linear inverse problem to be solved for image reconstruction can be solved in a more comfortable way leading to better results.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit may fulfill the functions of several means recited in the claims. Any reference signs in the claims shall not be construed as limiting the claim concerned.

REFERENCE NUMERALS

1 MIT system
2 tissue
3 measuring unit
4 generator coil
5 sensor coil
6 actuator
7 actuator 8 control unit
9 computer system
10 (free)
11 actuator
12 sensor coil axis
13 generator coils axis
14 rotation direction of generator coil
15 rotation direction of sensor coil
16 rotation axis
17 offset
18 z-axis
19 first measuring position
20 second measuring position
21 center of the measuring unit
22 horizontal plane
23 first horizontal direction
24 second horizontal direction

The invention claimed is:

1. A magnetic induction tomography system for studying electromagnetic properties of an object, the system comprising:
   one or more generator coils adapted for generating a primary magnetic field, said primary magnetic field inducing an eddy current in the object, one or more sensor coils adapted for sensing a secondary magnetic field, said secondary magnetic field being generated as a result of said eddy current, and
   actuators configured to provide a relative movement between at least one of the one or more generator coils and the one or more sensor coils on one hand and the object on another hand,
   wherein the at least one of the one or more generator coils and the one or more sensor coils are arranged in an asymmetric way such that a generator coil of the one or more generator coils is asymmetric with respect remaining generator coils of the one or more generator coils, or a sensor coil of the one or more sensor coils is asymmetric with respect remaining sensor coils of the one or more sensor coils.

2. The system as claimed in claim 1, wherein the at least one of the one or more generator coils and one or more sensor coils are arranged in form of an array.

3. The system as claimed in claim 1, wherein the actuators configured to move at least one of the one or more generator coils and the one or more sensor coils independent of each other.

4. The system as claimed in claim 1, wherein the actuators configured to rotate the at least one of the one or more generator coils and the one or more sensor coils relative to the object.

5. The system as claimed in claim 4, wherein the actuators configured to move the at least one of the one or more generator coils and the one or more sensor coils along the rotation axis.

6. The system as claimed in claim 1, further comprising an actuator configured to move the object relative to the at least one of the one or more generator coils and the one or more sensor coils, wherein the actuator is configured to rotate the object.

7. The system as claimed in claim 1, further comprising an actuator configured to move the object from a first measurement position to a second measurement position in a plane relative to the at least one of the one or more generator coils and/or relative to the one or more sensor coils.

8. The system as claimed in claim 1, further comprising an actuator configured to move the at least one of the one or more generator coils and the one or more sensor coils from a first measurement position to a second measurement position in a plane relative to the object.

9. The system as claimed in claim 1, wherein the one or more generator coils comprise at least two different generator coils, and the one or more sensor coils comprise at least two different sensor coils.

10. The system of claim 1, wherein at least one generator coil of the one or more generator coils has a size different from a size of a further generator coil of the one or more generator coils.

11. The system of claim 10, wherein at least one sensor coil of the one or more sensor coils has a size different from a size of a further sensor coil of the one or more sensor coils.

12. A magnetic induction tomography method for studying electromagnetic properties of an object, the method comprising the acts of:
   generating a primary magnetic field by one or more generator coils, said primary magnetic field inducing an eddy current in the object;
   sensing a secondary magnetic field by one or more sensor coils, said secondary magnetic field being generated as a result of said eddy; and
   providing a relative movement between at least one of the one or more generator coils and/or and the one or more sensor coils on one hand and the object on another hand,
   wherein the at least one of the one or more generator coils and the one or more sensor coils are arranged in an asymmetric way such that a generator coil of the one or more generator coils is asymmetric with respect remaining generator coils of the of the one or more generator coils, or a sensor coil of the one or more sensor coils is asymmetric with respect remaining sensor coils of the one or more sensor coils.

13. The method of claim 12, wherein at least one generator coil of the one or more generator coils has a size different from a size of a further generator coil of the one or more generator coils.

14. The system of claim 13, wherein at least one sensor coil of the one or more sensor coils has a size different from a size of a further sensor coil of the one or more sensor coils.

15. A tangible computer readable medium embodying non-transitory computer instructions for operating a magnetic induction tomography system for studying electromagnetic properties of an object, the non-transitory computer instructions being operative to cause a processor to perform the acts of:
   generating a primary magnetic field by one or more generator coils, said primary magnetic field inducing an eddy current in the object;
   sensing a secondary magnetic field by one or more sensor coils, said secondary magnetic field being generated as a result of said eddy; and
   providing a relative movement between at least one of the one or more generator coils and/or and the one or more sensor coils on one hand and the object on another hand,
   wherein the at least one of the one or more generator coils and the one or more sensor coils are arranged in an asymmetric way such that a generator coil of the one or more generator coils is asymmetric with respect remaining generator coils of the of the one or more generator coils, or a sensor coil of the one or more sensor coils is asymmetric with respect remaining sensor coils of the one or more sensor coils.

* * * * *